(12) United States Patent
Trejo et al.

(10) Patent No.: US 8,926,952 B2
(45) Date of Patent: Jan. 6, 2015

(54) METHODS OF USE OF PROBIOTIC BIFIDOBACTERIA FOR HUMAN BEAUTY BENEFITS

(75) Inventors: Amy Violet Trejo, Mason, OH (US); Liam Diarmuid O'Mahony, Co. Cork (IE)

(73) Assignees: The Procter & Gamble Company, Cincinnati, OH (US); Alimentary Health Limited, Country Cork (IE)

( * ) Notice: Subject to any disclaimer, the term of this patent is extended or adjusted under 35 U.S.C. 154(b) by 2103 days.

(21) Appl. No.: 11/398,943

(22) Filed: Apr. 6, 2006

(65) Prior Publication Data

US 2007/0031393 A1 Feb. 8, 2007

Related U.S. Application Data

(60) Provisional application No. 60/669,620, filed on Apr. 8, 2005.

(51) Int. Cl.
| | |
|---|---|
| A61K 8/00 | (2006.01) |
| A61K 8/18 | (2006.01) |
| A01N 63/00 | (2006.01) |
| C12N 1/20 | (2006.01) |
| A23L 1/30 | (2006.01) |
| A61K 8/99 | (2006.01) |
| A61K 35/74 | (2006.01) |
| A61Q 19/00 | (2006.01) |

(52) U.S. Cl.
CPC .............. *A23L 1/3014* (2013.01); *A61K 8/99* (2013.01); *A61K 35/745* (2013.01); *A61Q 19/00* (2013.01); *A61K 2800/92* (2013.01); *Y10S 435/822* (2013.01)
USPC ....... 424/70.1; 424/93.4; 435/252.1; 435/822

(58) Field of Classification Search
None
See application file for complete search history.

(56) References Cited

U.S. PATENT DOCUMENTS

| | | | |
|---|---|---|---|
| 4,464,362 A | 8/1984 | Kludas et al. | |
| 6,270,811 B1 | 8/2001 | Fregonese | |
| 2004/0258645 A1* | 12/2004 | Trejo et al. | 424/70.13 |
| 2005/0123500 A1 | 6/2005 | Trejo et al. | |

FOREIGN PATENT DOCUMENTS

| | | |
|---|---|---|
| EP | 1609463 A1 | 12/2005 |
| EP | 1642570 A1 | 4/2006 |
| WO | WO-00/42168 A2 | 7/2000 |
| WO | WO-03/010297 A1 | 2/2003 |
| WO | WO-03/070203 A1 | 8/2003 |
| WO | WO-03/070260 A1 | 8/2003 |
| WO | WO-2005/030230 A1 | 4/2005 |

OTHER PUBLICATIONS

International Search Report, PCT/US2006/013261, dated Aug. 18, 2006 (7 pages).
Isolauri E. et al., "Probiotics in the management of Atopic Eczema," Nov. 2000, Clinical and Experimental Allergy, Blackwell Scientific Publications, London, GB, pp. 1604-1610, XP001064231.

* cited by examiner

*Primary Examiner* — Debbie K Ware
(74) *Attorney, Agent, or Firm* — John G. Powell

(57) ABSTRACT

Methods of use in humans of probiotic bacteria of the genus *Bifidobacteria* for regulating the condition of human keratinous tissue to achieve cosmetic beauty benefits. Said methods include regulation, either prophylactic or therapeutic, of the cosmetic appearance of human keratinous tissue, such as human hair, skin (e.g., scalp), and nails. In another aspect, the invention provides a method of marketing a composition comprising probiotic *Bifidobacteria*. In one embodiment, the method comprises: (1) offering for sale a composition comprising probiotic *Bifidobacteria*; and (2) communicating to a potential consumer of said composition that oral administration of said composition can regulate the condition of human keratinous tissue.

10 Claims, No Drawings

METHODS OF USE OF PROBIOTIC BIFIDOBACTERIA FOR HUMAN BEAUTY BENEFITS

CROSS REFERENCE TO RELATED APPLICATION

This application claims the benefit of U.S. Provisional Application No. 60/669,620, filed Apr. 8, 2005 which is herein incorporated by reference in its entirety.

FIELD

The present invention relates to the field of probiotic *Bifidobacteria*, more specifically methods of use of probiotic *Bifidobacteria* for regulating the condition of human keratinous tissue to achieve cosmetic beauty benefits.

BACKGROUND

The defense mechanisms to protect the mammalian gastrointestinal (GI) tract from colonisation by bacteria are highly complex. The GI tract of most mammals are colonised by both native microflora and by invasive pathogenic microorganisms. In a healthy state, these competing microflora are in a state of equilibrium. The well being of humans is closely related to diet and GI health, and maintenance of the intestinal microflora equilibrium in humans can result in healthier human beings.

The number and composition of the intestinal microflora tend to be stable, although age and diet may modify it. Gastric acidity, bile, intestinal peristaltis and local immunity are factors thought to be important in the regulation of bacterial flora in the small intestine of human beings. Often human GI disorders are linked to bacterial overgrowth and the production of enterotoxins by pathogenic bacteria. These factors disrupt the intestinal microflora equilibrium and can promote inflammation and aberrant immune responses. Accordingly, modification of the intestinal microflora equilibrium may lead to or prevent many GI disorders.

Recently, research has begun to highlight some valuable strains of bacteria obtainable by isolation from the gastrointestinal tract of mammals, such as humans, and their potential use as probiotic agents. Probiotics are considered to be preparations of bacteria, either viable or dead, their constituents such as proteins or carbohydrates, or purified fractions of bacterial ferments that promote mammalian health by preserving the natural microflora in the GI tract, and reinforcing the normal controls on aberrant immune responses.

It is believed by some that probiotic bacteria are more effective when derived from the species, or closely related species, intended to be treated. While several strains of probiotic bacteria have been elucidated, methods of use of these strains and their therapeutic efficacy has largely been limited to modulation of gastro-intestinal disorders in humans. As yet, there has not been much investigation into the potential for these organisms to beneficially affect physiological systems other than the gastrointestinal tract.

BRIEF DESCRIPTION

According to the present invention, there is provided methods of use of probiotic *Bifidobacteria*, particularly those obtainable by isolation from the human gastrointestinal tract. Said methods include regulation, either prophylactic or therapeutic, of the cosmetic appearance of human keratinous tissue, such as human hair, skin (e.g., scalp), and nails.

In another aspect, the invention provides a method of marketing a composition comprising probiotic *Bifidobacteria*. In one embodiment, the method comprises: (1) offering for sale a composition comprising probiotic *Bifidobacteria*; and (2) communicating to a potential consumer of said composition that oral administration of said composition can regulate the cosmetic appearance of human keratinous tissue.

These and other features, aspects and advantages of the present invention will become evident to those skilled in the art from reading the present disclosure.

DETAILED DESCRIPTION

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Except where specific examples of actual measured values are presented, numerical values referred to herein should be considered to be qualified by the word "about".

Within the following description, the abbreviation CFU ("colony-forming unit") designates the number of bacterial cells revealed by microbiological counts on agar plates, as will be commonly understood in the art.

As used herein, the term "mutants thereof" includes derived bacterial strains having at least 88% homology, preferably at least 90% homology, more preferably 95% homology to the 16s-23s intergenic spacer polynulceotide sequence of a referenced strain, but otherwise comprising DNA mutations in other DNA sequences in the bacterial genome.

As used herein, the term "DNA mutations" includes natural or induced mutations comprising at least single base alterations including deletions, insertions, transversions, and other DNA modifications known to those skilled in the art, including genetic modification introduced into a parent nucleotide or amino acid sequence whilst maintaining at least 50% homology to the parent sequence. Preferably, the sequence comprising the DNA mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http://www.ncbi.nlm.nih.gov/BLAST/.

As used herein "genetic modification" includes the introduction of exogenous and/or endogenous DNA sequences into the genome of an organism either by insertion into the genome of said organism or by vectors including plasmid DNA or bacteriophage as known by one skilled in the art, said DNA sequence being at least two deoxyribonucleic acid bases in length.

As used herein, the term "probiotic" is broad enough to include one or more probiotics, one or more culture supernatants thereof, and/or mixtures thereof.

Bacterial Deposit Numbers

The table below sets forth the strain number and deposit/accession number for probiotic *Bifidobacteria* that can be useful in the present invention. The bacterial strains have been deposited with the National Collections of Industrial, Food and Marine Bacteria (NCIMB), Aberdeen, Scotland, UK.

| Strain Reference | NCIMB Deposit Number |
|---|---|
| AH208 | NCIMB 41050 |
| AH209 | NCIMB 41051 |
| AH210 | NCIMB 41052 |
| AH211 | NCIMB 41053 |
| AH212 | NCIMB 41099 |
| AH214 | NCIMB 41100 |
| AH35624 | NCIMB 41003 |

Probiotic *Bifidobacteria*

In particular embodiments, the probiotic *Bifidobacteria* used in practicing the present invention are selected from the group consisting of probiotic *Bifidobacteria* having accession number NCIMB 41050, NCIMB 41051, NCIMB 41052, NCIMB 41053, NCIMB 41099, NCIMB 41100, NCIMB 41003, mutants thereof, and mixtures thereof.

These probiotic *Bifidobacteria* are described in more detail in WO 00/42168 and WO 03/010297. WO 00/42168 describes probiotic *Bifidobacteria* isolated from the human GI tract. These bacteria are deposited at the NCIMB under deposit numbers 41050, 41051, 41052, 41053, 41099, and 41100. WO 03/010297 describes a further example of probiotic *Bifidobacteria* isolated from the human GI tract. This bacterium is deposited at the NCIMB under the deposit number 41003.

It has been found that strains of *Bifidobacteria* obtainable from the GI tract are adherent to the GI tract following the ingestion of viable bacterial cells, and are also significantly immunomodulatory when ingested in viable, non-viable or fractionated form. Without being bound by theory, it is believed that the *Bifidobacteria* obtainable from the GI tract closely associate with the gut mucosal tissues. Without further being bound by theory, this is believed to result in the probiotic *Bifidobacteria* generating alternative host responses that result in its probiotic action. It has been found that probiotic bacteria obtainable by isolation from the GI tract can modulate the host's immune system via direct interaction with the mucosal epithelium, and the host's immune cells. This immunomodulation, in conjunction with the traditional mechanism of action associated with probiotic bacteria, i.e., the prevention of pathogen adherence to the gut by occlusion and competition for nutrients, results in the *Bifidobacteria* being highly efficacious as a probiotic organism.

The *Bifidobacteria* useful in the present invention, obtainable by isolation from the human GI tract, have in vitro anti-microbial activity against a number of pathogenic bacterial strains/species. Without being bound by theory, it is believed that this in vitro anti-microbial activity is indicative of potential probiotic activity in vivo in humans.

Without being bound by theory, it is believed that the anti-microbial activity of the *Bifidobacteria* bacteria may be the result of a number of different actions by the *Bifidobacteria* bacteria. It has previously been suggested in the art that several strains of bacteria isolated from faecal samples exert their probiotic effect in the GI tract following oral consumption by preventing the attachment of pathogenic organisms to the gut mucosa by occlusion. This requires oral consumption of "live" or viable bacterial cells in order for a colony of bacteria to be established in the gut. However, it is believed that the *Bifidobacteria* useful in the present invention, obtainable by isolation from the human GI tract, whilst exerting some probiotic effect due to occlusion if given in a viable form, may deliver a substantial probiotic effect in either the viable or non-viable form due to the production during fermentation in vitro of a substance or substances that either inhibit the growth of or kill pathogenic micro-organisms, and/or alter the host human's immune competence. This form of probiotic activity is desirable, as the bacteria of the present invention can be given as either viable or non-viable cultures or purified fermentation products and still deliver a beneficial effect to the host.

Preferably, the *Bifidobacteria* bacteria are able to maintain viability following transit through the GI tract. This is desirable in order for live cultures of the bacteria to be taken orally, and for colonisation to occur in the intestines and bowel following transit through the oesophagus and stomach. Colonisation of the intestine and bowel by the probiotic *Bifidobacteria* of the present invention is desirable for long-term probiotic benefits to be delivered to the host. Oral dosing of non-viable cells or purified isolates thereof induces temporary benefits, but as the bacteria are not viable, they are not able to grow and continuously deliver a probiotic effect in situ. As a result this may require the host to be dosed regularly in order to maintain the health benefits. In contrast, viable cells that are able to survive gastric transit in the viable form, and subsequently colonise by adhering to and proliferating on the gut mucosa, are able to deliver probiotic effects continuously in situ.

Therefore, it is preferable that the *Bifidobacteria* of the present invention maintain viability after suspension in a media having a pH of 2.5 for 1 hour. As used herein, "maintain viability" means that at least 25% of the bacteria initially suspended in the test media are viable using the plate count method known to those skilled in the art. Preferably, "maintain viability" means that at least 50% of the bacteria initially suspended are viable. It is desirable for the *Bifidobacteria* of the present invention to maintain viability following exposure to low pH as this mimics the exposure to gastric juices in the stomach and upper intestine in vivo following oral consumption in humans.

Furthermore, it is preferable that the bacteria of the present invention have a growth of at least 33% when in the presence of at least 0.5% porcine bile salts. More preferably, the bacteria of the present invention have a growth of at least 33% when in the presence of at least 1% porcine bile salts. Without being bound by theory it is believed that the bacteria of the present invention, capable of maintaining viability in the presence of at least 0.5% porcine bile salts, are able to survive the conditions present in the intestine. This is thought to be a result of the addition of porcine bile to the culture medium mimicking the conditions of the intestine.

Further still, it is preferable that the *Bifidobacteria* bacteria useful in the present invention have significant adhesion to gut epithelial cells in vitro. As used herein, "significant adhesion" means at least 4% of the total number of bacteria co-incubated with the epithelial cells in vitro adhere to the epithelial cells. More preferably, at least 6% of bacterial cells co-incubated adhere to epithelial cells in vitro. Without being bound by theory, it is believed that gut epithelial cell adherence in vitro is indicative of the bacteria's ability to colonise the GI tract of a human in vivo.

The 16s-23s intergenic polynucelotide sequence is known to those skilled in the art as the sequence of DNA in the bacterial genome that can be used in order to identify different species and strains of bacteria. This intergenic polynucelotide sequence can be determined by the method detailed below.

*Bifidobacteria* colonies are picked from an Agar plate and resuspended in IX PCR buffer, heated at 96° C. for 5 minutes, frozen at −70° C. for 5-10 minutes, thawed and an aliquot is added to a PCR eppendorf tube. PCR is performed using the intergenic spacer (IGS) primers, IGS L: 5'-GCTGGATCAC-CTCCTTTC-3' SEQ NO ID: 1 and IGS R: 5'-CTGGTGC-CAAGGCATCCA-3' SEG NO ID: 2. The cycling conditions are 96° C. for 1 min (1 cycle), 94° C. for 30 sec, 53° C. for 30 sec, 72° C. for 30 sec (28 cycles). The PCR reaction contains 5 μl of DNA, PCR buffer (Bioline, UK), 0.2 mM dNTPs (Roche, UK), 0.4 μM IGS L and R primer (150 ng/50 μl) (MWG Biotech, Germany) and Bioline Taq polymerase (0.6 units). The PCR reactions are performed on a Hybaid thermocycler. The PCR products (8 μl) are run alongside a molecular weight marker (μX174 Hae III, Promega) on a 2% agarose EtBr stained gel in TAE, to determine their IGS profile. Using the same primers as above, the intergenic spacer (IGS) DNA is sequenced for *Bifidobacteria* strains using methods known to those skilled in the art.

Following sequencing, the obtained sequences for the strains can be compared with the on-line sequence database "BLAST", available at http://www.ncbi.nlm.nih.gov/BLAST/ for homology with other deposited bacterial 16s-23s sequences.

Methods of Use

According to the present invention, there is provided methods of use of probiotic *Bifidobacteria*, particularly those obtainable by isolation from the human gastrointestinal tract. Said methods include regulation, either prophylactic or therapeutic, of the cosmetic appearance of human keratinous tissue, such as human hair, skin (e.g., scalp), and nails.

In one aspect, the method comprises use of said probiotic *Bifidobacteria* for the purpose of regulating the cosmetic appearance of human keratinous tissue. In a particular aspect, the method comprises oral administration of said probiotic *Bifidobacteria* to a human for the purpose of regulating the cosmetic appearance of said human's keratinous tissue, wherein said human is seeking to regulate the cosmetic appearance of said human's keratinous tissue. In particular embodiments, regulating the condition of human keratinous tissue can comprise improving the cosmetic appearance of human keratinous tissue.

Preferably, the probiotic *Bifidobacteria* is orally administered in an effective amount, meaning in an amount sufficient to regulate the cosmetic appearance of human keratinous tissue. In a particular embodiment, the probiotic *Bifidobacteria* is orally administered daily, preferably daily for at least or about three months, and more preferably for at least or about one year.

In another aspect, the invention provides a method of marketing a composition comprising probiotic *Bifidobacteria*. In one embodiment, the method comprises: (1) offering for sale a composition comprising probiotic *Bifidobacteria*; and (2) communicating to a potential consumer of said composition that oral administration of said composition can regulate the condition of human keratinous tissue. In a particular embodiment, regulating the condition of human keratinous tissue comprises improving the cosmetic appearance of said human keratinous tissue.

As used herein, "communicating" means providing a message, and can include but is not limited to a printed (e.g., printed material attached directly or indirectly to a container that contains the composition), electronic, or broadcast message. As used herein, the term "potential consumer" means an actual or potential purchaser and/or an actual or potential user of the composition.

The probiotic *Bifidobacteria* of the present invention can be useful for regulating keratinous tissue (e.g., hair, skin [e.g., scalp], or nails) condition. As use herein, "regulating" or "regulation" means maintaining or improving the cosmetic appearance, and includes regulating visual, tactical, and kinesthetic properties of keratinous tissue, and can include prophylactically regulating and/or therapeutically regulating.

Regulation of keratinous tissue condition, in particular human skin, hair, or nail condition, is often desired due to conditions which may be induced or caused by factors internal and/or external to the body. Examples include environmental damage, radiation exposure (including ultraviolet radiation), chronological aging, menopausal status (e.g., post-menopausal changes in skin, hair, or nails), stress, diseases, disorders, etc.

For instance, "regulating skin, hair, or nail condition" includes prophylactically regulating and/or therapeutically regulating skin, hair, or nail condition, and may involve one or more of the following benefits: thickening of skin, hair, or nails (e.g., building the epidermis and/or dermis and/or subdermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (e.g., loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Regulating can also include smoothing, softening (e.g., of the skin), and reducing flaking of the skin and/or scalp. Regulating can include delaying, minimizing, preventing, ameliorating, and/or effacing undesired keratinous tissue conditions which may be detected visually, by feel, or otherwise. For instance, regulating can include regulating the signs of aging.

The term "sagging" as used herein means the laxity, slackness, or the like condition of skin that occurs as a result of loss of, damage to, alterations to, and/or abnormalities in dermal elastin, muscle and/or subcutaneous fat.

The terms "smoothing" and "softening" as used herein mean altering the surface of the keratinous tissue such that its tactile feel and/or overall look is improved.

The terms "signs of keratinous tissue aging" or "signs of aging" include, but are not limited to, all outward visibly and tactilely perceptible manifestations as well as any other macro or micro effects due to keratinous tissue aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, fine lines, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues (e.g., fat and/or muscle), especially those proximate to the skin.

The method of use of the *Bifidobacteria* bacteria of the present invention typically involves oral consumption by the human. Oral consumption may take place as part of the normal dietary intake, or as a supplement thereto. The oral consumption typically occurs at least once a month, preferably at least once a week, more preferably at least once per day. The *Bifidobacteria* may be administered by the human in an effective, preferably in a safe and effective, amount to regulate the condition of keratinous tissue of the human. As used herein, the term "safe and effective amount" with reference to the *Bifidobacteria*, means that amount of the bacteria sufficient to provide the desired effect or benefit to the human in need of treatment, yet low enough to avoid adverse effects such as toxicity, irritation, or allergic response, commensurate with a reasonable benefit/risk ratio when used in the manner of the present invention. The specific "safe and effective amount" will vary with such factors as the particular condition being treated, the physical condition of the user, the duration of the treatment, the nature of concurrent therapy (if any), the specific dosage form to be used, the carrier employed, the solubility of the dose form, and the particular dosing regimen.

Preferably, the *Bifidobacteria* are administered to the human at a dose of from 1.0E+04 to 1.0E+14 CFU per day, more preferably from 1.0E+06 to 1.0E+12 CFU per day. The composition preferably may contain at least 0.001% of from 1.0E+04 to 1.0E+12 CFU/g of the *Bifidobacteria* obtainable by isolation from the human GI tract. The *Bifidobacteria* bacteria can be given to the human in either viable form, or as killed cells, or distillates, isolates or other fractions of the fermentation products of the *Bifidobacteria* of the present invention, or any mixture thereof.

Preferably, the *Bifidobacteria* bacteria, or a purified or isolated fraction thereof, are used to prepare a composition intended to regulate the cosmetic appearance of human keratinous tissue. As indicated above, the composition may be part of the normal dietary intake, or a supplement. Where the composition comprises part of the normal dietary intake, the composition may be in the form of a tablet, capsule, food, candy, yogurt, powder, beverage, and the like. Such compositions may comprise further components.

The compositions comprising the bacteria of the present invention may also comprise a prebiotic. "Prebiotic" includes substances or compounds that are fermented by the intestinal flora of the human and hence promote the growth or development of *Bifidobacteria* in the gastro-intestinal tract of the human at the expense of pathogenic bacteria. The result of this fermentation is a release of fatty acids, in particular short-chain fatty acids in the colon. This has the effect of reducing the pH value in the colon. Non-limiting examples of suitable prebiotics include oligosaccharides, such as inulin and its hydrolysis products commonly known as fructooligosaccharides, galacto-oligosaccharides, xylo-oligosaccharides or oligo derivatives of starch. The prebiotics may be provided in any suitable form. For example, the prebiotic may be provided in the form of plant material which contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti SA of Tirlemont 3300, Belgium under the trade mark "Raftiline". For example, the inulin may be provided in the form of Raftiline (g) ST which is a fine white powder which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti SA of Tirlemont 3300, Belgium under the trade mark "Raftilose". For example, the inulin may be provided in the form o Raftilose (g) P95. Otherwise, the fructooligosaccharides may be obtained by hydrolyzing inulin, by enzymatic methods, or by using micro-organisms.

The foods may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids and docosahexanoic acid.

Borage oil, blackcurrent seed oil and evening primrose oil are suitable sources of gamma linolenic acid. Safflower oils, sunflower oils, corn oils and soy bean oils are suitable sources of linoleic acid. These oils may also be used in the coating substrates referred to above. Zinc may be provided in various suitable forms, for example as zinc sulfate or zinc oxide.

EXAMPLES

The following examples further describe and demonstrate embodiments within the scope of the present invention. They are given for the purpose of illustration and are not to be construed as limitations of the present invention. Where applicable, ingredients are given in CTFA name.

| Ex. | Material | Water Activity | Water Content (%) | Weight (%) |
|---|---|---|---|---|
| 1 | Freeze Dried *B. Infantis* ($5 \times 10^{12}$ CFU/g) | 0.04 | 6 | 50 |
|   | Microcrystalline Cellulose | 0.04 | <1.5 | 50 |
| 2 | Freeze Dried *B. Infantis* ($1 \times 10^{10}$ CFU/g) | 0.04 | 6 | 25 |
|   | Potato Starch | 0.09 | <6 | 75 |
| 3 | Freeze Dried *B. Infantis* ($1 \times 10^{11}$ CFU/g) | 0.04 | 6 | 40 |
|   | Psyllium hemicellulose | 0.05 | <8 | 60 |
| 4 | Freeze Dried *L. Salivarius* ($5 \times 10^{12}$ CFU/g) | 0.04 | 5 | 80 |
|   | Microcrystalline Cellulose | 0.04 | 1 | 20 |
| 5 | Freeze Dried *L. Acidophilus* ($3 \times 10^{11}$ CFU/g) | 0.04 | 5 | 60 |
|   | Maltodextrin | 0.25 | 5 | 39.5 |
|   | Magnesium Stearate | 0.41 | <6 | 0.5 |
| 6 | Freeze Dried *B. Infantis* ($1 \times 10^{11}$ CFU/g) | 0.04 | 6 | 45 |
|   | Potato Starch | 0.09 | <6 | 39.25 |
|   | Magnesium Stearate | 0.41 | <6 | 0.75 |
|   | Ascorbic Acid | — | — | 15 |

-continued

| Ex. | Material | Water Activity | Water Content (%) | Weight (%) |
|---|---|---|---|---|
| 7 | Freeze Dried *B. Infantis* ($2 \times 10^{12}$ CFU/g) | 0.04 | 6 | 15 |
|  | Freeze Dried *L. Salivarius* ($2 \times 10^{12}$ CFU/g) | 0.04 | 5 | 15 |
|  | Microcrystalline Cellulose | 0.04 | <1.5 | 27 |
|  | Fumed Silica | — | — | 2 |
|  | Magnesium Stearate | 0.41 | <6 | 1 |
|  | Ascorbic Acid | — | — | 20 |
|  | Tricalcium citrate | — | — | 20 |
| 8 | Freeze Dried *B. Infantis* ($5 \times 10^{11}$ CFU/g) | 0.04 | 6 | 30 |
|  | Freeze Dried *L. Salivarius* ($5 \times 10^{11}$ CFU/g) | 0.04 | 5 | 30 |
|  | Microcrystalline Cellulose | 0.04 | <1.5 | 23 |
|  | Fumed Silica | — | — | 1 |
|  | Magnesium Stearate | 0.41 | <6 | 1 |
|  | Ascorbic Acid | — | — | 5 |
|  | Calcium lactate gluconate | — | — | 10 |

The above examples are dry bacteria compositions prepared according to the following procedure. All operations are performed in a humidity-controlled environment where the RH is maintained between 30 and 36%. The appropriate amount of freeze-dried bacteria (pre-concentrated to the desired CFU/g) are added to the mixing cavity of a Pharmatech mixer along with the appropriate amount of stabiliser such as microcrystalline cellulose, potato starch or the like. The bacteria and stabilisers have been chosen for their low water activity and low water content as well as similar particle size and densities to allow for more efficient mixing. The head space within the mixing cavity is flushed with dry Nitrogen gas such that the gasses of the original headspace have been replaced a total of 10 times or until the RH inside the mixing cavity is reduced to below 20%. The mixing cavity is then sealed with an airtight lid and the powders mixed together for 20 minutes at a rotation speed of 60 rpm. Once mixing has finished the stability of the powder blend can be maintained by ensuring the powders are not exposed to high RH's (greater than 36% RH) or water-rich environments. The dry-blended powders can be packaged into gelatin capsules under a nitrogen/low RH environment and stored in sealed containers or as dry powders in sachets or containers. The resulting capsules and powders contained therein have improved long-term stability both at low temperatures (4° C.) and room temperature (25° C.).

In a further embodiment, the dry bacteria compositions of examples 1 to 8 can be packaged into unit dose forms such as capsules or sachets under a nitrogen/low (<36%) relative humidity (RH) environment. Examples 9 to 11 demonstrate non-limiting examples of unit dose compositions packaged in and packaged into capsules. The capsules are intended to be taken as a single dose, swallowed whole. Examples 12 to 14 are non-limiting examples of unit dose compositions packaged into sachets, providing higher bacteria counts per dose when compared with the capsules.

| Example | Packaging Format | Dry Bacteria Composition | CFU per dose |
|---|---|---|---|
| 9 | Gelatin Capsule | 100 mg of Ex. 1 | $2.5 \times 10^{11}$ |
| 10 | HPMC Capsule | 180 mg of Ex. 2 | $4.5 \times 10^{8}$ |
| 11 | Gelatin Capsule | 250 mg of Ex. 5 | $1 \times 10^{12}$ |
| 12 | Sachet | 2 g of Ex. 7 | $1.2 \times 10^{12}$ |
| 13 | Sachet | 5 g of Ex. 8 | $1.5 \times 10^{12}$ |
| 14 | Sachet | 1 g of ex. 4 | $4 \times 10^{12}$ |

Examples 15 to 17 are examples of yogurt supplement compositions comprising the probiotic *Bifidobacteria globosum*.

| | Percentage on a weight Basis | | |
|---|---|---|---|
| Ingredient | Ex. 15 | Ex. 16 | Ex. 17 |
| Milk | 38 | 42 | 48 |
| Sugar | 12 | 12 | 10 |
| Modified Starch | 1.0 | 0.8 | 0.8 |
| Prebiotic | 0.25 | 0.3 | 0.5 |
| Probiotic NCIMB 41052 ($1 \times 10^{10}$ CFU/g) | 4 | 5 | 6 |

Examples 18 to 20 are examples of methods of marketing compositions comprising probiotic *Bifidobacteria*.

| Example No. | Composition Offered for Sale | Communication |
|---|---|---|
| 18 | Gelatin capsules of Example 9 are packaged in a bottle and offered for sale to potential consumers on a shelf in the beauty aisle of a retail drug store | Printed matter attached to the bottle states that consumption of the capsules can help to make hair look more shiny and vibrant |

-continued

| Example No. | Composition Offered for Sale | Communication |
| --- | --- | --- |
| 19 | Sachets of Example 14 are offered for sale to potential consumers on a shelf in the beauty aisle of a health food store | A television advertisement states that oral administration of the sachets can help to reduce the visible signs of skin aging and can help make nails less brittle |
| 20 | Yogurt supplements of Example 17 are packaged in containers and offered for sale to potential consumers on a shelf in the dietary supplements aisle at a grocery store | A print advertisement in a magazine states that consumption of the yogurt supplement can help reduce flaking of the scalp |

All publications cited herein are hereby incorporated by reference in their entirety; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern. All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of regulating the condition of human keratinous tissue, comprising orally administering a probiotic strain of *Bifidobacteria* to a human seeking said regulation.

2. The method of claim 1, wherein said *Bifidobacteria* is isolated from the human gastrointestinal tract.

3. The method of claim 1, wherein said *Bifidobacteria* is selected from the group consisting of *Bifidobacteria* having accession numbers NCIMB 41050, NCIMB 41051, NCIMB 41052, NCIMB 41053, NCIMB 41099, NCIMB 41100, NCIMB 41003, mutants thereof, and mixtures thereof.

4. The method of claim 1, wherein said human keratinous tissue is human skin.

5. The method of claim 1, wherein said human keratinous tissue is human scalp.

6. The method of claim 1, wherein said human keratinous tissue is human nails.

7. The method of claim 1, wherein said human keratinous tissue is human hair.

8. A method of regulating the condition of human keratinous tissue, consisting of orally administering a probiotic strain of *Bifidobacteria* to a human seeking said regulation.

9. A method of regulating the condition of human keratinous tissue, comprising orally administering a probiotic strain of *Bifidobacteria* to a human seeking said regulation at a dose of at least about 2 grams per day.

10. A method of regulating the condition of human keratinous tissue, comprising orally administering a probiotic strain of *Bifidobacteria* to a human seeking said regulation, wherein the probiotic strain of *Bifidobacteria* is contained in a unit dose form within a sachet.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 1
gctggatcac ctcctttc                                                 18

<210> SEQ ID NO 2
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 2
ctggtgccaa ggcatcca                                                 18
```